US011007054B2

(12) United States Patent
Braido et al.

(10) Patent No.: US 11,007,054 B2
(45) Date of Patent: May 18, 2021

(54) SUBANNULAR SEALING FOR PARAVALVULAR LEAK PROTECTION

(71) Applicant: St. Jude Medical, Cardiology Division, Inc., St. Paul, MN (US)

(72) Inventors: Peter N. Braido, Wyoming, MN (US); Kent J. Smith, Shoreview, MN (US); Andrea L. McCarthy, Vadnais Heights, MN (US); Andrea N. Para, Highlands Ranch, CO (US); Sounthara Khouengboua, Chaska, MN (US); Thomas M. Benson, Minneapolis, MN (US); Saravana B. Kumar, Minnetonka, MN (US); Bruce Moseman, Belle Plaine, MN (US); Gaurav Satam, Falcon Heights, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 189 days.

(21) Appl. No.: 16/110,231

(22) Filed: Aug. 23, 2018

(65) Prior Publication Data

US 2019/0000617 A1  Jan. 3, 2019

Related U.S. Application Data

(62) Division of application No. 15/310,915, filed as application No. PCT/US2015/030358 on May 12, 2015, now Pat. No. 10,130,467.

(Continued)

(51) Int. Cl.
*A61F 2/24* (2006.01)

(52) U.S. Cl.
CPC .... *A61F 2/2418* (2013.01); *A61F 2210/0014* (2013.01); *A61F 2220/0075* (2013.01);
(Continued)

(58) Field of Classification Search
USPC .................................................. 623/1.1–3.1
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 10121210 B4 | 11/2002 |
| DE | 19857887 B4 | 5/2005 |

(Continued)

OTHER PUBLICATIONS

"Closed heart surgery: Back to the future", Samuel V. Lichtenstein, The Journal of Thoracic and Cardiovascular Surgery, vol. 131, No. 5, pp. 941-943.

(Continued)

*Primary Examiner* — Yashita Sharma
(74) *Attorney, Agent, or Firm* — Lerner, David, Littenberg, Krumholz & Mentlik, LLP

(57) ABSTRACT

A prosthetic heart valve for replacing a native valve includes a collapsible and expandable stent extending between a proximal end and a distal end. The stent includes an annulus section adjacent the proximal end and having a first diameter, a plurality of first struts forming cells, and a plurality of second struts connected to the annulus section and forming a plurality of deflecting cells expandable to define a second diameter larger than the first diameter. A valve assembly is disposed within the stent and a cuff is coupled to the stent and covers the plurality of deflecting cells.

13 Claims, 15 Drawing Sheets

Related U.S. Application Data

(60) Provisional application No. 61/994,271, filed on May 16, 2014.

(52) U.S. Cl.
CPC . *A61F 2230/001* (2013.01); *A61F 2230/0013* (2013.01); *A61F 2250/0036* (2013.01); *A61F 2250/0069* (2013.01); *H05K 999/99* (2013.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| D684,692 S | 6/2013 | Braido |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |

(56) References Cited

U.S. PATENT DOCUMENTS

| | | |
|---|---|---|
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0020327 A1* | 1/2006 | Lashinski ............ A61F 2/2439 623/1.25 |
| 2006/0058872 A1 | 3/2006 | Salahieh et al. |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097571 A1* | 4/2008 | Denison ............... A61F 2/844 623/1.11 |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Sun et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0256723 A1 | 10/2010 | Murray |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2013/0282113 A1 | 10/2013 | Punga et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0277423 A1 | 9/2014 | Alkhatib et al. |
| 2014/0303719 A1 | 10/2014 | Cox et al. |
| 2014/0316516 A1 | 10/2014 | Vidlund et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |
| 2015/0265394 A1* | 9/2015 | Cragg ............... A61F 2/07 623/1.35 |
| 2015/0320556 A1* | 11/2015 | Levi ............... A61F 2/2427 623/2.11 |

FOREIGN PATENT DOCUMENTS

| | | |
|---|---|---|
| DE | 202008009610 U1 | 12/2008 |
| DE | 10003632 A1 | 1/2010 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| EP | 2537487 A1 | 12/2012 |
| FR | 2 847 800 B1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |

(56) References Cited

FOREIGN PATENT DOCUMENTS

| WO | 0236048 | A1 | 5/2002 |
|---|---|---|---|
| WO | 0247575 | A2 | 6/2002 |
| WO | 02067782 | A2 | 9/2002 |
| WO | 03047468 | A1 | 6/2003 |
| WO | 2005070343 | A1 | 8/2005 |
| WO | 06073626 | A2 | 7/2006 |
| WO | 2007071436 | A2 | 6/2007 |
| WO | 08070797 | A2 | 6/2008 |
| WO | 2010008548 | A2 | 1/2010 |
| WO | 2010008549 | A1 | 1/2010 |
| WO | 2010096176 | A1 | 8/2010 |
| WO | 2010098857 | A1 | 9/2010 |
| WO | 2013103612 | A1 | 7/2013 |

OTHER PUBLICATIONS

"Direct-Access Valve Replacement", Christoph H. Huber, et al., Journal of the American College of Cardiology, vol. 46, No. 2, (Jul. 19, 2005).

"Minimally invasive cardiac surgery", M. J. Mack, Surgical Endoscopy, 2006, 20:S488-S492, DOI: 10.1007/s00464-006-0110-8 (presented Apr. 24, 2006).

"Percutaneous Aortic Valve Implantation Retrograde From the Femoral Artery", John G. Webb et al., Circulation, 2006; 113:842-850 (Feb. 6, 2006).

"Transapical aortic valve implantation: an animal feasibility study"; Todd M. Dewey et al., The annals of thoracic surgery 2006; 82: 110-6 (Feb. 13, 2006).

"Transapical approach for sutureless stent-fixed aortic valve implantation: experimental results"; Th. Walther et al., European Journal of Cardio-thoracic Surgery 29 (2006) 703-708 (Jan. 30, 2006).

"Transapical Transcatheter Aortic Valve Implantation in Humans", Samuel V. Lichtenstein et al., Circulation. 2006; 114: 591-596 (Jul. 31, 2006).

Braido et al., U.S. Appl. No. 29/375,243, filed Sep. 20, 2010, titled "Surgical Stent Assembly".

Buellesfeld, et al., "Treatment of paravalvular leaks through inverventional techniques," Multimed Man Cardiothorac Surg., Department of Cardiology, Ben University Hospital, pp. 1-8, Jan. 2011.

Catheter-implanted prosthetic heart valves, Knudsen, L.L., et al., The International Journal of Artificial Organs, vol. 16, No. 5 1993, pp. 253-262.

De Cicco, et al., "Aortic valve periprosthetic leakage: anatomic observations and surgical results," The Annals of thoracic surgery, vol. 79, No. 5, pp. 1480-1485, May 2005.

Gössl, et al., "Percutaneous treatment of aortic and mitral valve paravalvular regurgitation," Current Cardiology Reports, vol. 15, No. 8., pp. 1-8, Aug. 2013.

Heart Advisor, "Heart repairs without surgery. Minimally invasive procedures aim to correct valve leakage," Sep. 2004, pp. 4-5, PubMed ID 15586429.

International Search Report for International Patent Application No. PCT/US2015/030358 dated Apr. 8, 2015.

Is It Reasonable to Treat All Calcified Stenotic Aortic Valves With a Valved Stent?, 579-584, Zegdi, Rachid, MD, PhD at al., J. of the American College of Cardiology, vol. 51, No. 5, Feb. 5, 2008.

Moazami, N. et al., "Transluminal Aortic Valve Placement," ASAIO Journal, Sep./Oct. 1996, pp. M381-M385, vol. 42.

Muñoz, et al., "Guidance of treatment of perivalvular prosthetic leaks.", Current cardiology reports, 16.430, 6 pages, Jan. 2014.

Percutaneous aortic valve replacement: resection before implantation, 836-840, Quaden, Rene et al., European J. of Cardio-thoracic Surgery, 27 (2005).

Rohde, et al., "Resection of Calcified Aortic Heart Leaflets In Vitro by Q-Switched 2 μm Microsecond Laser Radiation", Journal of Cardiac Surgery, 30(2):157-62. Feb. 2015.

Ruiz, Carlos, Overview of PRE-CE Mark Transcatheter Aortic Valve Technologies, Euro PCR May 25, 2010.

Swiatkiewicz, et al., "Percutaneous closure of mitral perivalvular leak," Kardiologia Polska, vol. 67, No. 7, pp. 762-764, Jul. 2009.

Textbook "Transcatheter Valve Repair", 2006, pp. 165-186.

Transcatheter Umbrella Closure of Valvular and Paravalvular Leaks, Hourihan et al., Journal of the American College of Cardiology, vol. 20, No. 6, pp. 1371-1377, (1992).

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

* cited by examiner

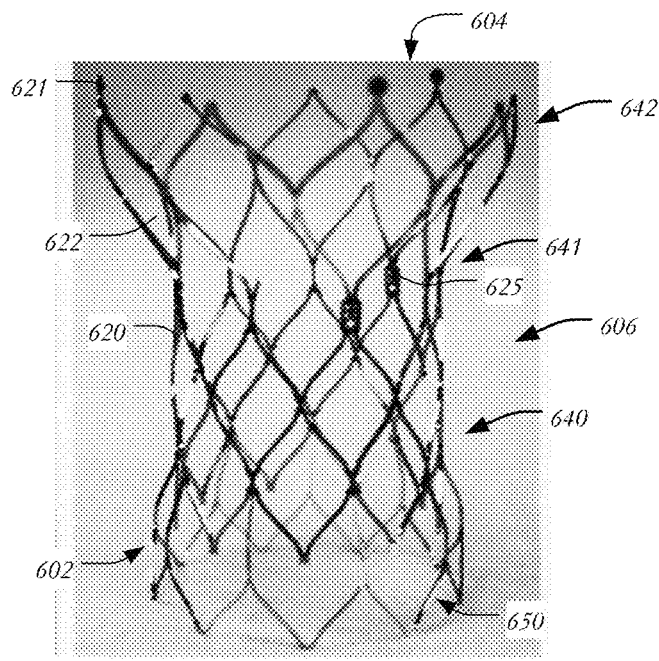
FIG. 6A
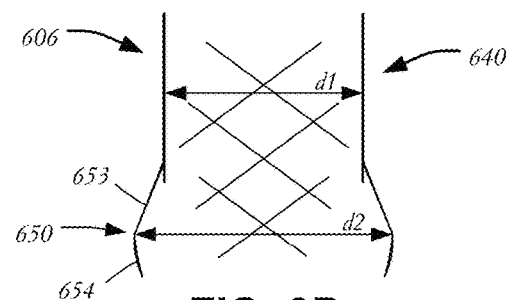
FIG. 6B
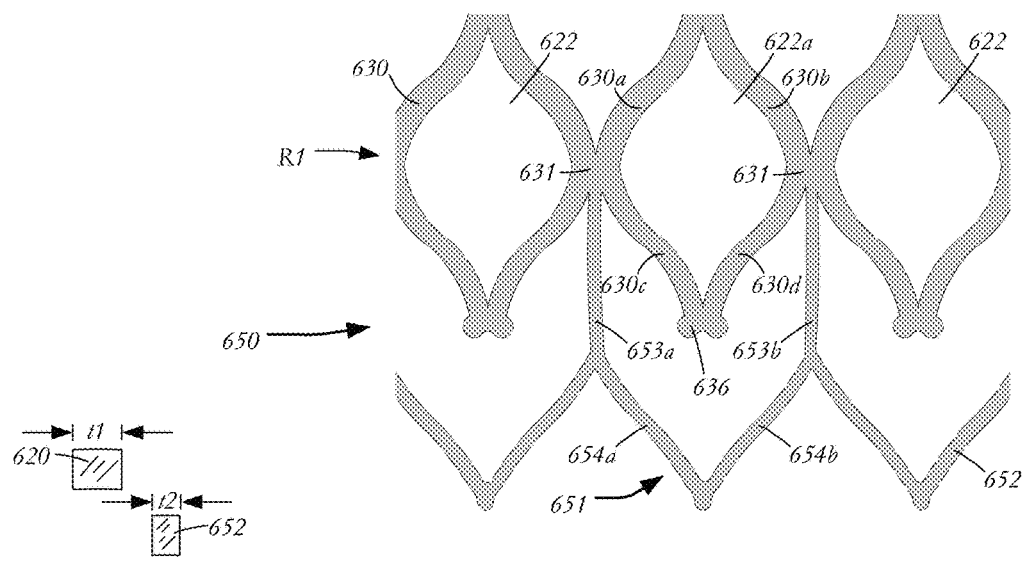
FIG. 6D
FIG. 6C

SUBANNULAR SEALING FOR PARAVALVULAR LEAK PROTECTION

CROSS-REFERENCE TO RELATED APPLICATIONS

The present application is a divisional of U.S. patent application Ser. No. 15/310,915, filed Nov. 14, 2016, which is a national phase entry under 35 U.S.C. § 371 of International Application No. PCT/US2015/030358 filed May 12, 2015, published in English, which claims the benefit of the filing date of U.S. Provisional Patent Application No. 61/994,271 filed May 16, 2014, the disclosures of which are all hereby incorporated herein by reference.

The present disclosure relates in general to heart valve replacement and, in particular, to collapsible prosthetic heart valves. More particularly, the present disclosure relates to devices and methods for positioning and sealing collapsible prosthetic heart valves within a native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve for replacing a native valve includes a collapsible and expandable stent extending between a proximal end and a distal end. The stent includes an annulus section adjacent the proximal end and having a first diameter, a plurality of first struts forming cells, and a plurality of second struts connected to the annulus section and forming a plurality of deflecting cells expandable to define a second diameter larger than the first diameter. A valve assembly is disposed within the stent and a cuff is coupled to the stent and covers the plurality of deflecting cells.

In some embodiments, a prosthetic heart valve for replacing a native valve includes a collapsible and expandable stent extending between a proximal end and a distal end and an annulus section adjacent the proximal end and having a first diameter. The stent includes a plurality of first struts forming cells, and a plurality of projecting struts joined to proximal-most cells, each of the projecting struts having a free end and an attached end joined to an intersection of first struts. A valve assembly is disposed within the stent and a cuff is coupled to the stent and covering the projecting struts.

In some embodiments, a prosthetic heart valve for replacing a native heart valve includes a collapsible and expandable stent having proximal and distal ends, the stent including an annulus section adjacent the proximal end, the annulus section having a first expanded diameter and a first radial spring constant. The stent further includes a plurality of deflecting features which project outwardly from the annulus section when the stent is in an expanded condition, the deflection features having a lower radial spring constant than the first section. A valve is disposed within the annulus section distal to the deflection features, the valve being operative to permit flow toward the distal end of the stent and to substantially block flow toward the proximal end of the stent. The heart valve further includes a cuff, a portion of the cuff being coupled to the deflection features.

BRIEF DESCRIPTION OF THE DRAWINGS

Various embodiments in accordance with the present disclosure will now be described with reference to the appended drawings. It is to be appreciated that these drawings depict only some embodiments and are therefore not to be considered limiting of its scope.

FIG. 6A is a side view of a stent having a sealing row of deflecting cells;

FIG. 6B is a highly schematic partial cross-sectional view of the annulus section of the stent of FIG. 6A;

FIG. 6C is a schematic partial side view of the stent of FIG. 6A;

FIG. 6D are schematic cross-sectional views of the struts of FIG. 6A;

DETAILED DESCRIPTION

Inaccurate deployment and anchoring may result in the leakage of blood between the implanted heart valve and the native valve annulus, commonly referred to as paravalvular leakage (also known as "perivalvular leakage"). In aortic valves, this leakage enables blood to flow from the aorta back into the left ventricle, reducing cardiac efficiency and putting a greater strain on the heart muscle. Additionally, calcification of the aortic valve and/or anatomical variations from one patient to another may affect performance and the interaction between the implanted valve and the calcified tissue is believed to be relevant to leakage, as will be outlined below. There is a need for further improvements to the devices, systems, and methods for positioning and sealing collapsible prosthetic heart valves. Specifically, there is a need for further improvements to the devices, systems, and methods for accurately implanting a prosthetic heart valve. Among other advantages, the present disclosure may address one or more of these needs.

As used herein, the terms "proximal" and "distal" when used in connection with a prosthetic heart valve, refer to the inflow and outflow ends, respectively, of the heart valve corresponding to natural circulation of blood through a healthy heart. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user.

Figure 1:
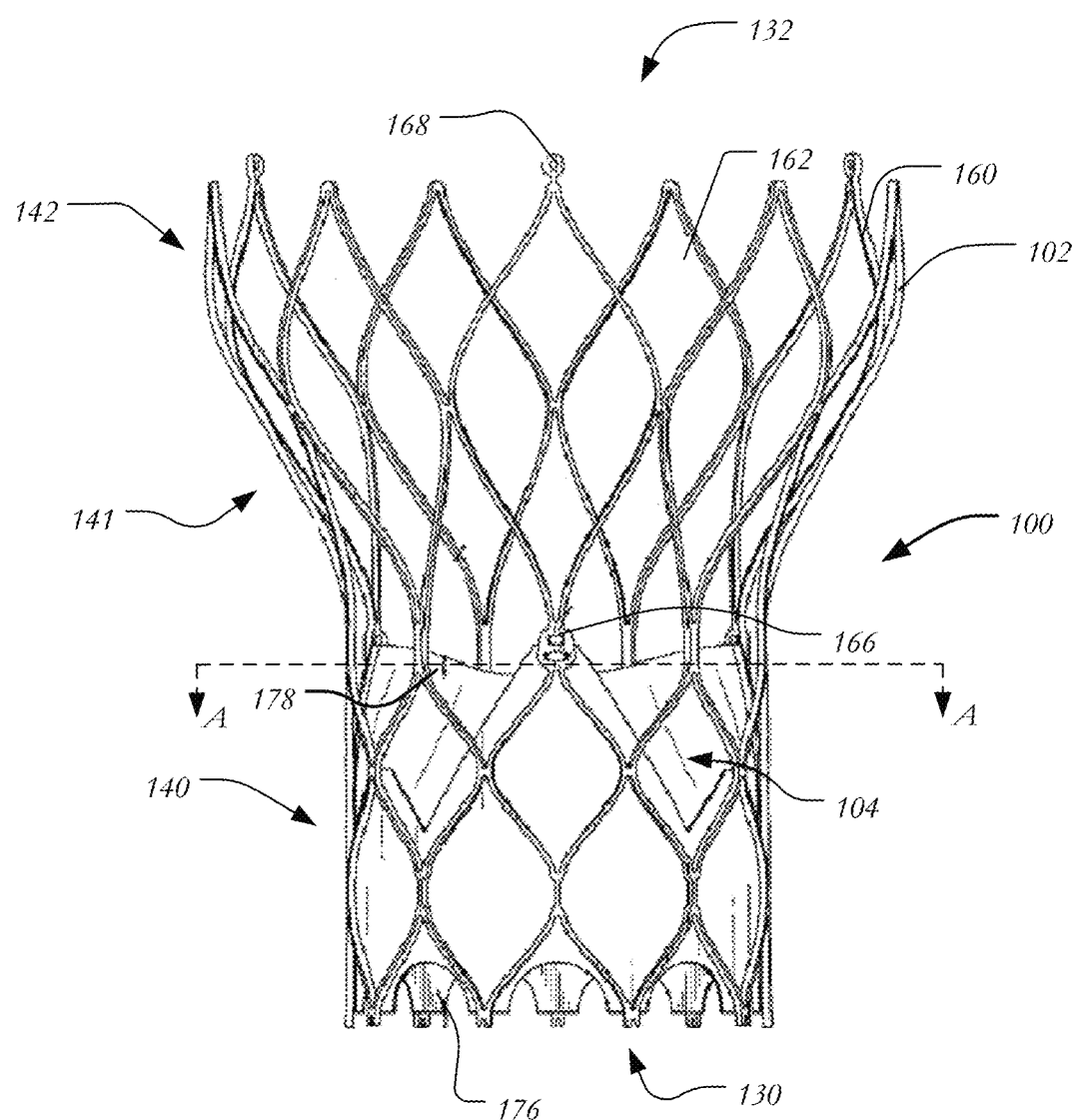
FIG. 1 is a side elevational view of a conventional prosthetic heart valve.

The sealing features of the present disclosure may be used in connection with collapsible prosthetic heart valves. FIG. 1 shows one such collapsible stent-supported prosthetic heart valve 100 including a stent 102 and a valve assembly 104 as is known in the art. Prosthetic heart valve 100 is designed to replace a native tricuspid valve of a patient, such as a native aortic valve. It should be noted that while the embodiments discussed herein relate predominantly to prosthetic aortic valves having a stent with a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 (FIG. 1) includes expandable stent 102 which may be formed from biocompatible materials that are capable of self-expansion, such as, for example, shape memory alloys, such as the nickel-titanium alloy known as "Nitinol" or other suitable metals or polymers. Stent 102 extends from proximal or annulus end 130 to distal or aortic end 132, and includes annulus section 140 adjacent proximal end 130, transition section 141 and aortic section 142 adjacent distal end 132. Annulus section 140 may have a relatively small cross-section in the expanded configuration, while aortic section 142 may have a relatively large cross-section in the expanded configuration. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may include one or more retaining elements 168 at distal end 132 thereof, retaining elements 168 being sized and shaped to cooperate with female retaining structures (not shown) provided on a deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104 preferably secured to stent 102 in annulus section 140. Valve assembly 104 includes cuff 176 and a plurality of leaflets 178 which collectively function as a one-way valve by coapting with one another. As a prosthetic aortic valve, valve 100 has three leaflets 178. However, it will be appreciated that other prosthetic heart valves with which the sealing portions of the present disclosure may be used may have a greater or lesser number of leaflets.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed of any suitable biological material or polymer such as, for example, Polyethylene terephthalate (PET), ultra-high-molecular-weight polyethylene (UHMWPE), or polytetrafluoroethylene (PTFE).

Leaflets 178 may be attached along lower belly portions to cells 162 of stent 102, with the commissure between adjacent leaflets 178 attached to commissure features 166. As can be seen in FIG. 1, each commissure feature 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to stent 102.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed configuration. The delivery device may be introduced into a patient using a transfemoral, transaortic, transsubclavian, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Figure 2:
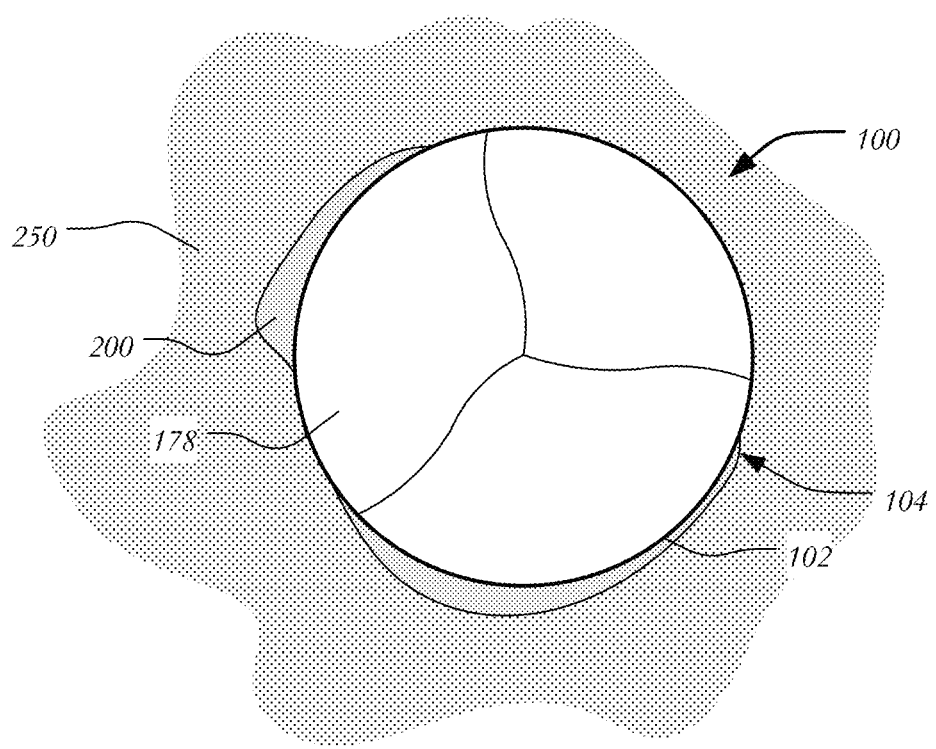
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, valve assembly 104 has a substantially circular cross-section which is disposed within the non-circular native valve annulus 250. It will be understood that while prosthetic heart valve 100 is shown having a circular cross-section for the sake of clarity, certain portions will deflect to accommodate the geometry in the anatomy. Additionally, heart valve 100 may include an elliptical or D-shaped cross-section for use in mitral, tricuspid, or diseased bicuspid valve applications. At certain locations around the perimeter of heart valve 100, gaps 200 form between heart valve 100 and native valve annulus 250. Blood flowing through these gaps and past valve assembly 104 of prosthetic heart valve 100 can cause regurgitation and other inefficiencies which reduce cardiac performance. Such improper fitment may be due to suboptimal native valve annulus geometry due, for example, to calcification of native valve annulus 250 or to irregularities in unresected native leaflets.

Figure 3A:
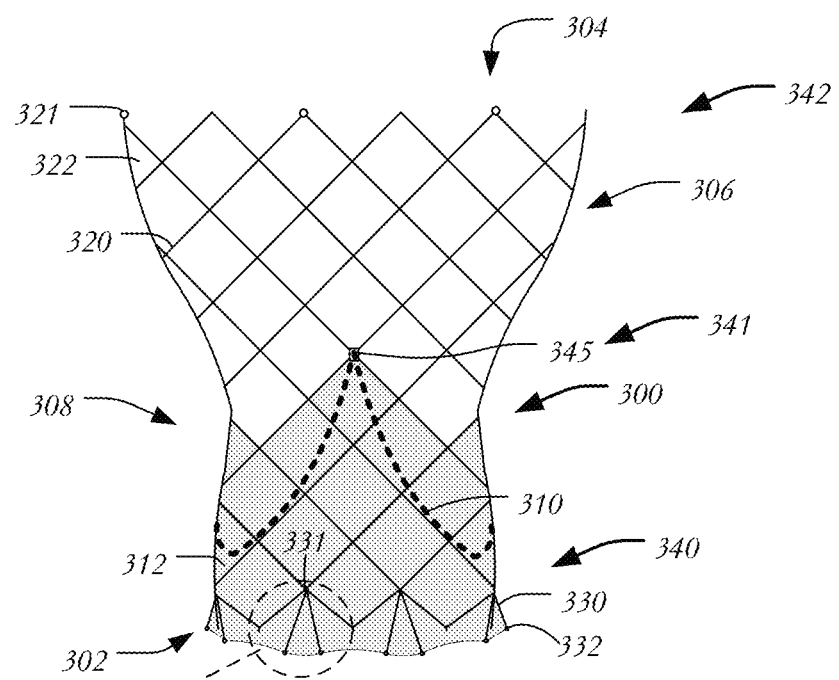
FIG. 3A is a highly schematic side view of one embodiment of a heart valve having projecting struts intended to fill irregularities between the heart valve and the native valve annulus.

FIG. 3A illustrates one embodiment of heart valve 300 intended to fill the irregularities between the heart valve and native valve annulus 250 shown in FIG. 2. Heart valve 300 extends between proximal end 302 and distal end 304, and may generally include stent 306 and valve assembly 308 having a plurality of leaflets 310 and cuff 312. Heart valve 300 may be formed of any of the materials and in any of the configurations described above with reference to FIG. 1.

Stent 306 may include a plurality of struts 320 and extend from proximal or annulus end 302 of heart valve 300 to distal or aortic end 304. Stent 306 may include annulus section 340 adjacent proximal end 302, aortic section 342 adjacent distal end 304, and transition section 341 between annulus section 340 and aortic section 342. Commissure features 345 may be positioned entirely within annulus section 340 or at the juncture of annulus section 340 and transition section 341 as shown.

Figure 3B:
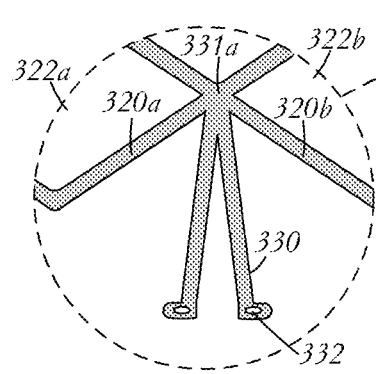
FIG. 3B is a fragmentary view of an enlarged section of the portion indicated in FIG. 3A.

At distal end 304, certain struts 320 may terminate in retaining elements 321. Additionally, struts 320 may come together to form cells 322 connected to one another in one or more annular rows around the stent. Specifically cells 322 are diamond-shaped and include four intersections or nodes of struts 320. The functional features of valve 300 may be generally similar to the corresponding features of valve 100 discussed above. Adjacent the proximal-most full row of cells 322 additional features are included to reduce paravalvular leakage. These features are best described with reference to the enlargement shown in FIG. 3B. As shown, cells 322a and 322b are disposed adjacent to one another and share a common node 331a (e.g., struts 320a of cell 322a and 320b of adjacent cell 322b intersect at node 331a). A plurality of projecting struts 330 are provided, each projecting strut 330 including an attached end coupled to node 331a and a free end having eyelet 332. In this example, two projecting struts 330 extend from each node 331a. It will be understood, however, that a single projecting strut 330 or more than two projecting struts 330 may extend from each node. Additionally, projecting struts 330 need not extend from each node 331, but may be extend from less than all of the nodes. For example, projecting struts 330 may extend from alternating nodes around the circumference of heart valve 300.

Projected struts 330 may be biased to extend radially outward to define a diameter greater than the diameter of annulus section 340. In addition to the biasing, cuff 312 may be attached to eyelets 332 and expand radially outward with projecting struts 330 to better seal heart valve 300 within the native valve annulus.

Figure 3C:
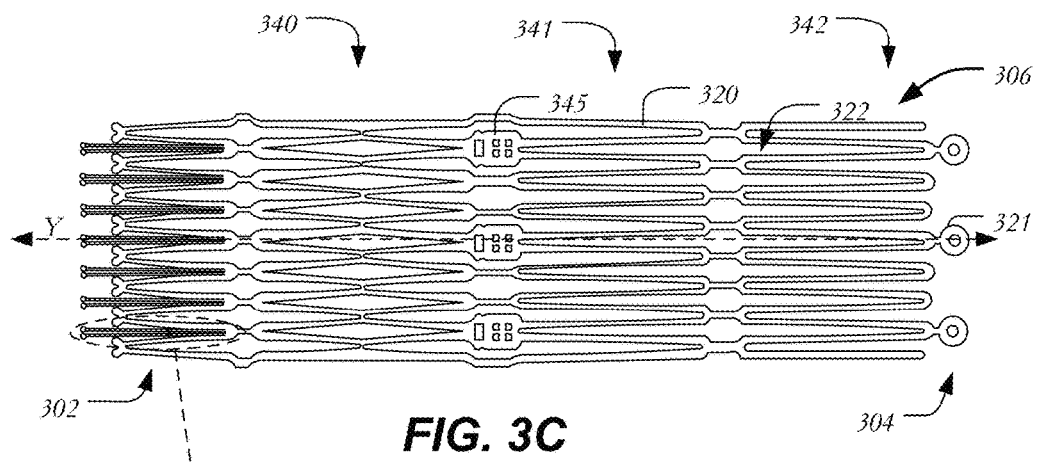
FIG. 3C is a developed view of the stent of the heart valve of FIG. 3A in the collapsed configuration.
Figure 3D:
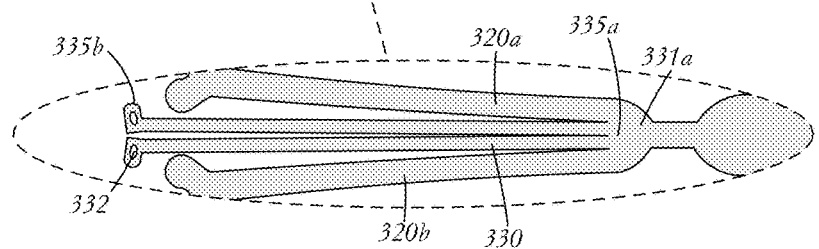
FIG. 3D is a fragmentary view of an enlarged section of the portion indicated in FIG. 3C.

In order to better appreciate the attachment and placement of projecting struts 330, stent 306 is shown in FIG. 3C in its collapsed configuration. A portion of the collapsed stent is shown in detail on an enlarged scaled in FIG. 3D. For the sake of clarity, valve assembly 308 is not shown in this figure. In the collapsed configuration of stent 306, cells 322 may be substantially stadium-shaped (e.g., having two parallel sides and two semi-circles connecting the parallel sides). This collapsed shape, however, may be modified as desired and may also change based on the amount of compression applied to the stent. In the expanded configuration of stent 306, cell 322 may shorten in the length direction of stent 306 between proximal end 302 and distal end 304, and struts 320 may generally form a diamond shape (FIG. 3A).

Projecting struts 330 may extend from first attached ends 335a, where struts 320a and 320c meet (e.g., node 331a), to free ends 335b. Attached ends 335a may be affixed to stent 306 by welding, adhesive, or any other suitable technique known in the art. Moreover, instead of being separately formed and affixed to stent 306 at nodes 331a, projecting struts 330 may be integrally formed with stent 306, such as by laser cutting both stent 306 and projecting struts 330 from the same tube.

Figure 3E:
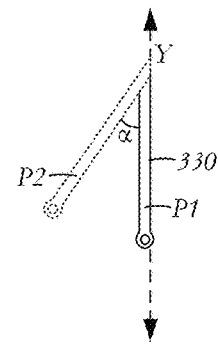
FIG. 3E is a schematic representation of the attachment angle of the projecting struts of FIG. 3A.

As seen in FIG. 3E, in the collapsed configuration, projecting struts 330 may be substantially parallel to longitudinal axis Y of heart valve 300 at position P1. As heart valve 300 expands, projecting struts 330 begin to angle outwardly, forming an angle α with longitudinal axis Y of heart valve 300 to position P2. In at least some examples, angle α is between about 15 degrees and about 35 degrees. It will be understood that angle α may, however, be greater than 35 degrees or less than 15 degrees as desired. Stent 306 may be formed such that struts 320 and projecting struts 330 return to a predetermined angled configuration in the fully expanded configuration due, for example, to elasticity of the projecting struts (e.g., when no external forces are applied thereto). When projecting struts 330 project outwardly to position P2 on the expansion of heart valve 300, they form protuberances in cuff 312 to help seal heart valve 300 within the native valve annulus. Additionally, though projecting struts 330 may be configured to deflect to a given angle when unconstrained (e.g., 35 degrees), it will be understood that in use, projecting struts 330 may outwardly deflect to an angle less than the maximum unconstrained angle (e.g., 20 degrees) due to the presence of calcium nodule or other anatomical structure. Moreover, in this configuration, projecting struts 330 may be capable of independent movement so that a first projecting struts 330 is capable of deflecting outwardly to a first angle α, while a second projecting strut 330 deflects to a smaller extent to accommodate a calcium nodule or other anatomical structure. Thus, it will be understood that cuff 312 need not expand to a circular circumference at projecting struts 330.

Figure 4A:
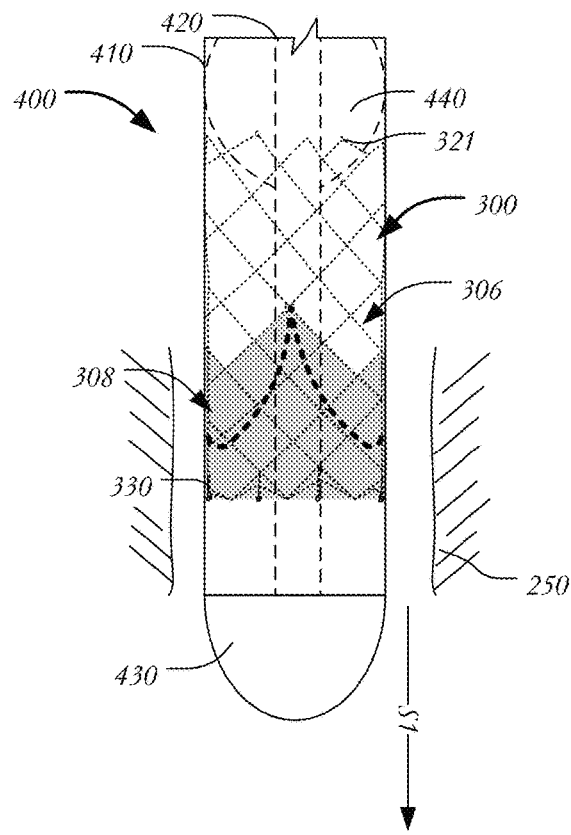
FIGS. 4A-D are highly schematic side views of one method of delivering and deploying the heart valve of FIG. 3A within the native valve annulus.

A method of delivering and implanting heart valve 300 will now be described with reference to FIGS. 4A-D. A delivery system 400 may be used to deliver and deploy heart valve 300 in native valve annulus 250, and may generally include sheath 410, shaft 420, atraumatic tip 430 and hub 440. Sheath 410 may be slidable relative to shaft 420. Heart valve 300, including stent 306, valve assembly 308 and projecting struts 330, may be disposed within sheath 410 about shaft 420 (FIG. 4A). Hub 440 may be coupled to shaft 420 and configured to mate with retaining elements 321 of heart valve 300. Projecting struts 330 of heart valve 300 may be substantially parallel to the longitudinal axis of sheath 410, during delivery. Specifically, though projecting struts 330 are configured to return to their angled configuration, they may be kept substantially parallel by being constrained within sheath 410. By doing so, heart valve 300 may be delivered to the native valve annulus using delivery system 400 without increasing the radius of sheath 410, avoiding the need to increase the crimp profile of the heart valve within delivery system 400 (i.e., the diameter of the heart valve in the collapsed condition). A large delivery system may be incapable of being passed through the patient's vasculature, while a delivery system having a heart valve with a smaller crimp profile may be easier to navigate through a patient's body and may also reduce the length of the implantation procedure. In the example shown in FIGS. 4A-D, delivery system 400 is delivered from the aorta toward the left ventricle as indicated by arrow 51. If heart valve 300 or delivery system 400 includes echogenic materials, such materials may be used to guide delivery system 400 to the appropriate position using the assistance of three-dimensional echocardiography to visualize heart valve 300 within the patient. Alternative visualization techniques known in the art are also contemplated herein.

Figure 4B:
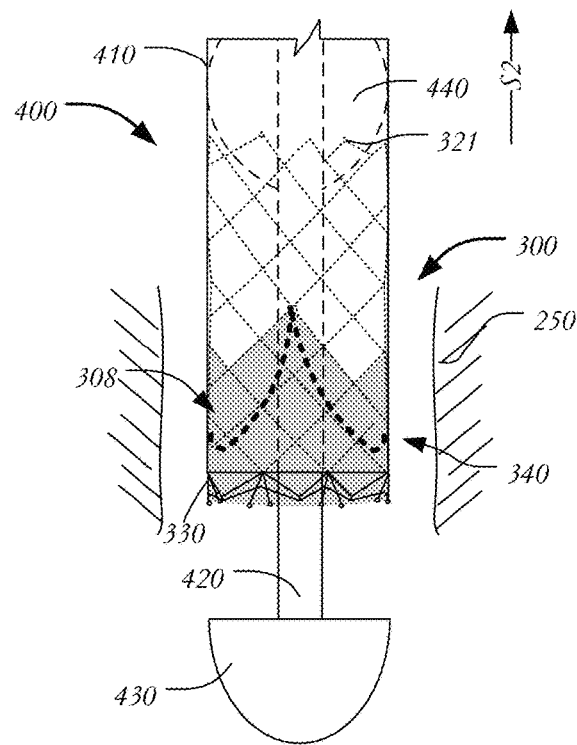
Figures 4C, 4D:
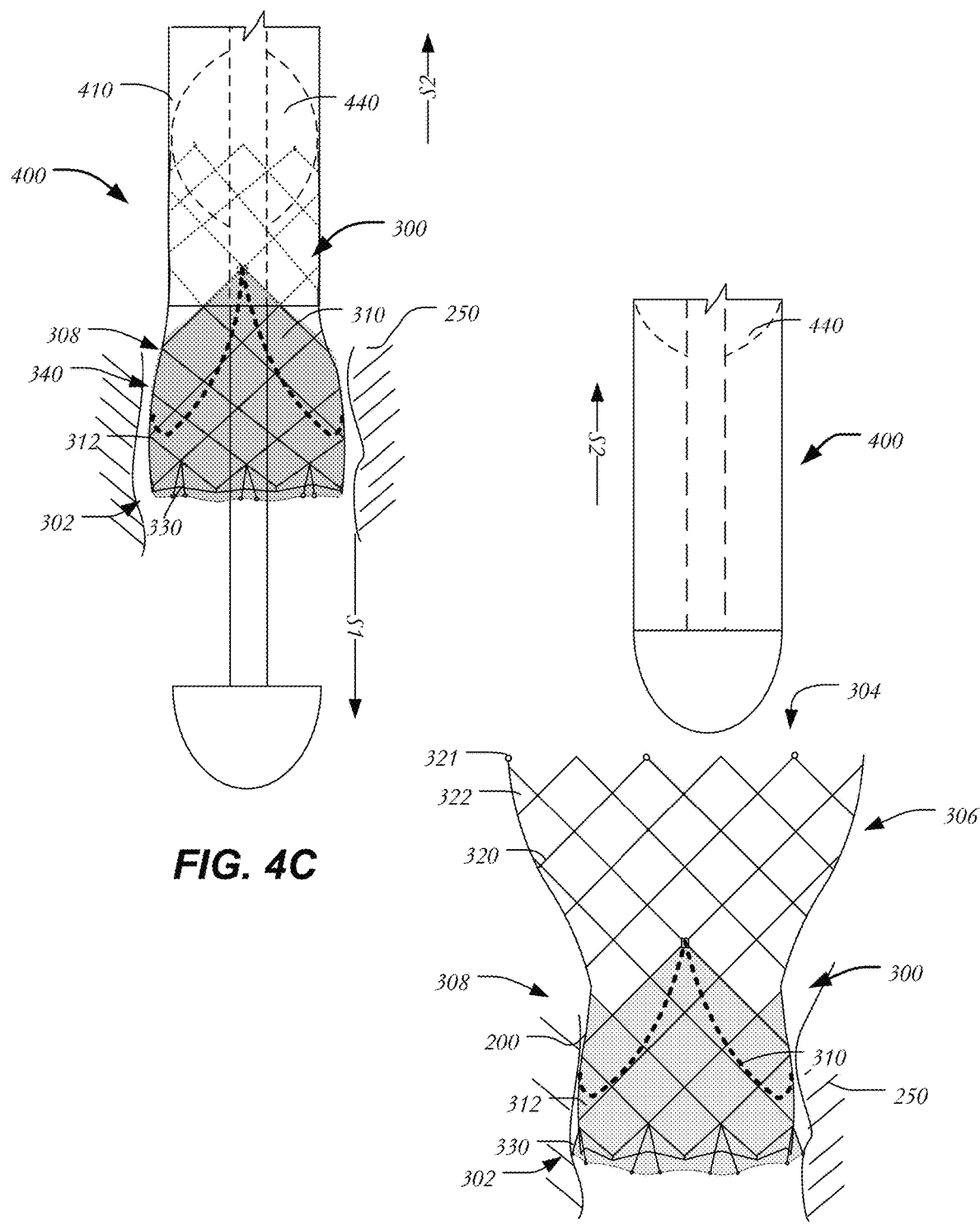

When delivery system 400 has reached the proper location (e.g., atraumatic tip 430 is just past native valve annulus 250), atraumatic tip 430 may be decoupled from sheath 410 (FIG. 4B). Sheath 410 may then be retracted in the direction of arrow S2 toward the aorta. With sheath 410 slightly retracted, heart valve 300 begins to emerge from the sheath. As sheath 410 is further retracted in the direction of arrow S2, more of heart valve 300 is exposed until annulus section 340 is fully exposed and projecting struts 330 begin to protrude outwardly (FIGS. 4B-C). Thus, sheath 410 may be retracted until heart valve 300 is free to self-expand within native valve annulus 250. While heart valve 300 is partially deployed (e.g., a portion of heart valve 300 is outside sheath 410, but heart valve 300 is not fully detached from delivery system 400), if it appears that heart valve 300 needs to be recaptured and redeployed due to, for example, improper positioning or orientation, sheath 410 may be slid over shaft 420 in the direction of arrow 51 to recapture heart valve 300 within sheath 410. During recapture, sheath 410 may push against projecting struts 330 to straighten them to the parallel configuration shown in FIG. 4A. This process may be repeated until heart valve 300 is properly positioned and deployed within native valve annulus 250.

After sheath 410 has been fully retracted to expose heart valve 300, projecting struts 330, now in their angled configuration, push cuff 312 outwardly against native valve annulus 250. The cuff occludes gaps 200 between heart valve 300 and native valve annulus 250, thereby reducing or eliminating the amount of blood that passes around heart valve 300 through gaps 200 (FIG. 4D). Retaining elements 321 of heart valve 300 may decouple from hub 440 as heart valve 300 fully expands, atraumatic tip 430 may be retracted through heart valve 300 in the direction of arrow S2 and delivery system 400 may be removed from the patient.

Figure 5:
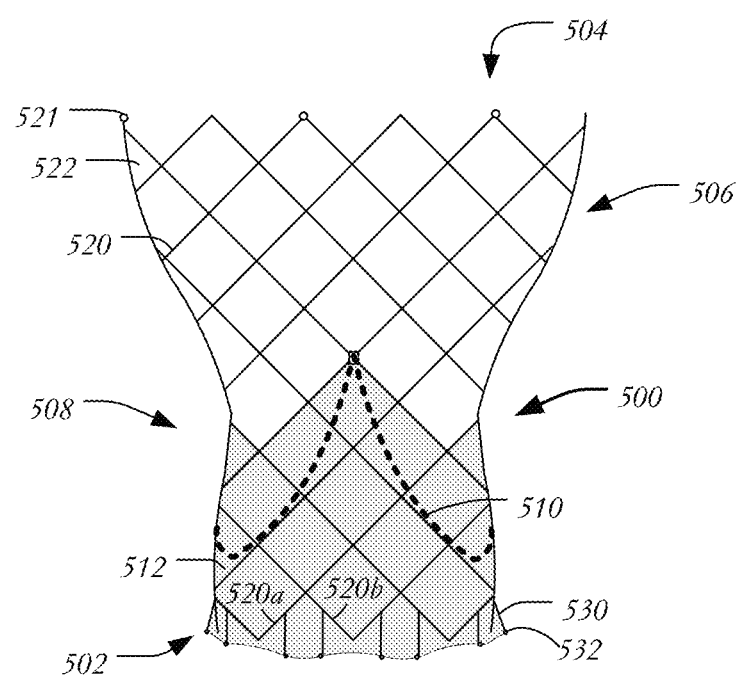
FIG. 5 is a highly schematic side view of another variation of a heart valve having projecting struts intended to fill irregularities between the heart valve and the native valve annulus.

FIG. 5 shows a variation of the embodiment described above with reference to FIGS. 3A-4D. Heart valve 500 extends between proximal end 502 and distal end 504 and includes stent 306 and a valve assembly 508 having leaflets 510 and cuff 512. Stent 506 includes a plurality of struts 520 forming cells 522 and having retaining elements 521 at the distal end of the heart valve as described above. Heart valve 500 further includes projecting struts 530 disposed near proximal end 502. In contrast to heart valve 300 of FIGS. 3A-C, projecting struts 530 are coupled to select struts 520 at locations remote from the nodes defined by intersecting struts. As shown, projecting struts 530 are coupled to the proximal-most struts 520a,520b approximately halfway between nodes. Each projecting struts 530 includes an eyelet 532 for coupling the strut to cuff 512. In use, heart valve 500 functions similar to heart valve 300 and projecting struts may alternate between a substantially parallel configuration for delivery to an angled configuration for sealing heart valve 500 within a native valve annulus.

Instead of projecting struts, additional rows of cells may be used to aid in paravalvular sealing. Stent 606 of FIGS. 6A-C illustrates one such embodiment. For the sake of clarity, a valve assembly (e.g., cuff and leaflets) is not shown in FIGS. 6A-C, though it will be understood that a valve assembly is coupled to stent 606 to form a functional heart valve. Stent 606 extends between proximal end 602 and distal end 604. Stent 606 includes a plurality of first struts 620 forming cells 622 and having retaining elements 621 at the distal end of the stent for delivery. Stent 606 may further include commissure features 625 to which portions of the leaflets and/or cuff are attached. Stent 606 may include three sections as previously described, including annulus section 640 adjacent proximal end 602, aortic section 642 adjacent distal end 604, and transition section 641 between annulus section 640 and aortic section 642. Commissure features 625 may be positioned entirely within annulus section 640 or at the juncture of annulus section 640 and transition section 641 as shown.

An additional sealing row 650 of cells is added to the proximal end 602 of stent 606. Sealing row 650, in its fully expanded condition may define a diameter that is larger than the diameter of annulus section 640 when stent 606 is expanded in the native valve annulus. Thus, as shown in FIG. 6B, the difference between the fully-expanded diameter d2 of sealing row 650 and the fully-expanded diameter d1 of annulus section 640 may be between about 4.0 mm to about 6.0 mm. In other words, sealing row 650 extends outwardly about 2.0 to 3.0 mm in each radial direction beyond annulus section 640. The difference between the fully-expanded diameter d2 of sealing row 650 and the fully-expanded diameter d1 of annulus section 640 may also be between about 2.0 mm to about 4.0 mm.

The details of sealing row 650 will be discussed in greater detail with reference to FIG. 6C. As shown, stent 606 includes a row R1 of diamond-shaped cells 622 formed by intersecting first struts 630. For example, cell 622a is formed by connecting first struts 630a-d. A blunt end 636 shaped as a horseshoe is formed at the intersection of the lowermost struts 630 (e.g., struts 630c and 630d of cell 622a). An additional sealing row 650 is formed proximal to row R1 of cells 622. Sealing row 650 may generally include a number of deflecting cells 651, each deflecting cell 651 being formed of slender struts 652 that have a thickness t2 that is smaller than the thickness t1 of first struts 630 (FIG. 6D). In at least some examples, first struts 630 are twice as thick as slender struts 652. In at least some examples, first struts 630 are formed with a thickness of about 0.25 to about 0.50 mm or about 0.40 mm to about 0.50 mm, and slender struts are formed with a thickness of about 0.1 to about 0.2 mm or between about 0.15 mm to about 0.20 mm. The reduced thickness of slender struts 652 may provide increased flexibility and allow them to more readily bend to form outwardly projecting sealing row 650. Slender struts 652 further allow deflecting cells 651 to be conformable to patient anatomy as well as calcium nodules, if present.

Sealing row 650 of deflecting cells 651 may have a spring constant that is less than the spring constant of annulus section 640. In other words, sealing row 650 may be made more conformable than annulus section 640. Annulus section 640 may be formed flexible enough to conform to the patient's anatomy yet rigid enough to provide adequate anchoring of the valve assembly within the native valve annulus. Conversely, deflecting cells 651 may provide little anchoring of the valve but are more conformable to accommodate calcium nodules and the native anatomical structures, such as unresected leaflets in order to minimize paravalvular leakage.

Deflecting cells 651 may be formed of two upper struts 653a,653b and two lower struts 654a,654b. Each of upper struts 653 are coupled at one end to nodes 631 of adjacent cells 622 and two lower struts 654a,654b at the other end. In addition to being coupled to upper struts 653a,653b respectively, lower struts 654a,654b are coupled to each other. As schematically shown in FIG. 6B, upper struts 653 are angled outwardly from annulus section 640 to define a second, larger diameter d2 of sealing row 650. Upper struts 653 may be about 9.0 mm to about 10.0 mm in length. When implanted, a portion of stent 606 may extend below the native valve annulus and the length of upper struts 653 will be partially responsible for the amount of deflecting cells 651 that protrudes below the annulus. Generally, the longer the upper strut, the more deflecting cell 651 will extend below the native valve annulus. For example, with a 9.0 mm length of upper struts 653, approximately 1.0 mm to 6.0 mm of deflecting cell 651 protrudes below the native valve annulus, depending on the overall geometry of cell 651.

Moreover, in addition to diameter, several factors may be modified in order to form the desired shape for paravalvular leakage prevention including the lengths of struts 653,654 and the shape of deflecting cells 651. Such variations will be described in greater detail with reference to FIGS. 7-8.

Figure 7A:
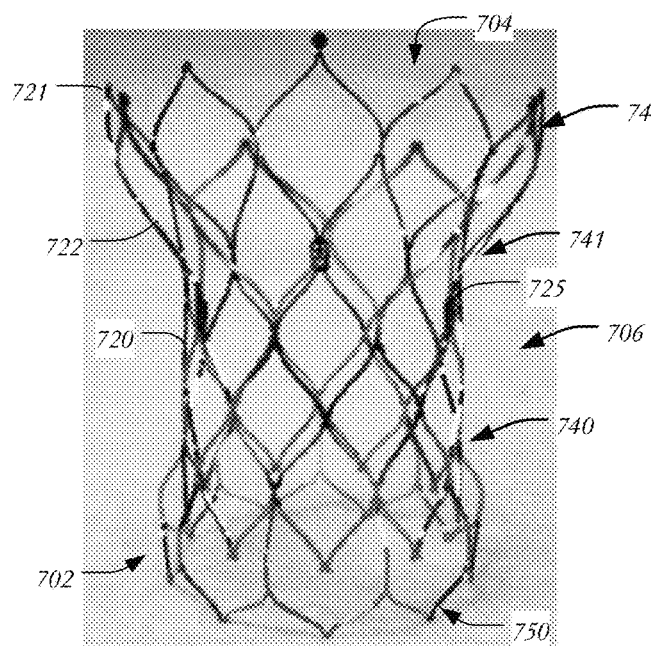
FIG. 7A is a side view of another variation of a stent having a sealing row of deflecting cells.
Figure 7B:
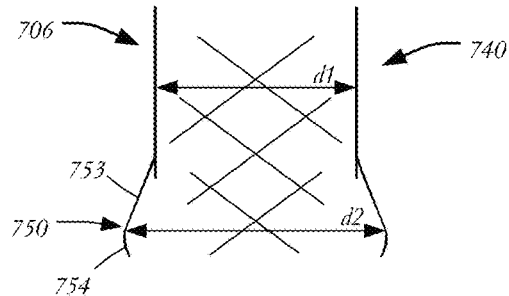
FIG. 7B is a highly schematic partial cross-sectional view of the annulus section of the stent of FIG. 7A.
Figure 7C:
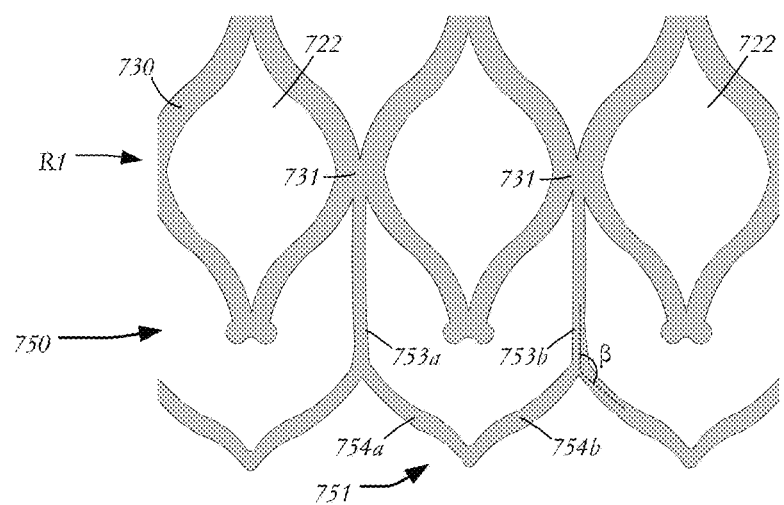
FIG. 7C is a schematic partial side view of the stent of FIG. 7A.

FIGS. 7A-C illustrate a variation of stent 606 of FIGS. 6A-C. Stent 706 extends between proximal end 702 and distal end 704 and includes a plurality of struts 720 forming cells 722 and having retaining elements 721 at the distal end of the stent. Stent 706 may further include commissure features 725 and may be divided into roughly three sections as previously described, including annulus section 740 adjacent proximal end 702, aortic section 742 adjacent distal end 704, and transition section 741 between annulus section 740 and aortic section 742. An additional sealing row 750 of deflecting cells 751 having an expanded diameter as described earlier is formed.

The principle difference between stent 606 and stent 706 is in the shape of defecting cells 751. Deflecting cells 751 may be formed of two upper struts 753a,753b and two lower struts 754a,754b. Each of upper struts 753 are coupled at one end to node 731 of adjacent cells 722 and two lower struts 754a,754b at the other end. In addition to being coupled to upper struts 753a,753b respectively, lower struts 754a,754b are coupled to each other. Upper struts 753 may be formed of the same length as upper struts 653 (e.g., about 9.0 mm to about 10.0 mm in length). In order to reduce the portion of deflecting cells 651 extending below the native valve annulus, lower struts 754a,754b may be attached to upper struts 753a,753b at an angle β that is smaller than the attachment angle of stent 606. In at least some examples, the angle β may be between about 90 degrees and about 145 degrees. In other examples, the angle β may be between less than 90 degrees or greater than 145 degrees. Additionally, lower struts 754a,754b may be slightly shortened to accommodate this difference in attachment angle.

Figure 8A:
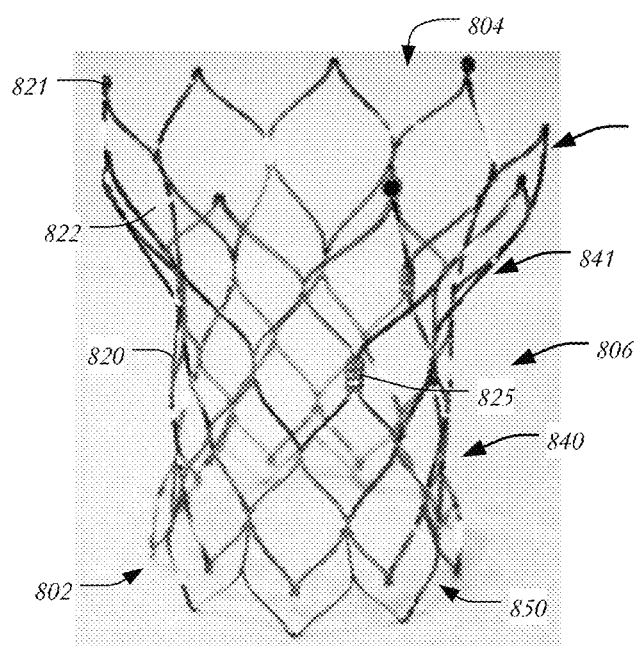
FIG. 8A is a side view of another variation of a stent having a sealing row of deflecting cells.
Figure 8B:
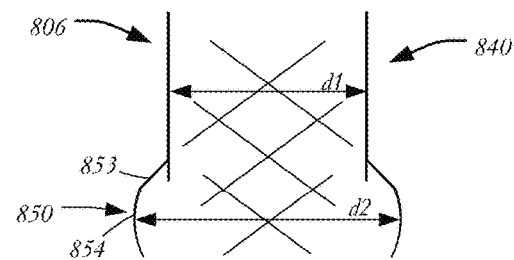
FIG. 8B is a highly schematic partial cross-sectional view of the annulus section of the stent of FIG. 8A.
Figure 8C:
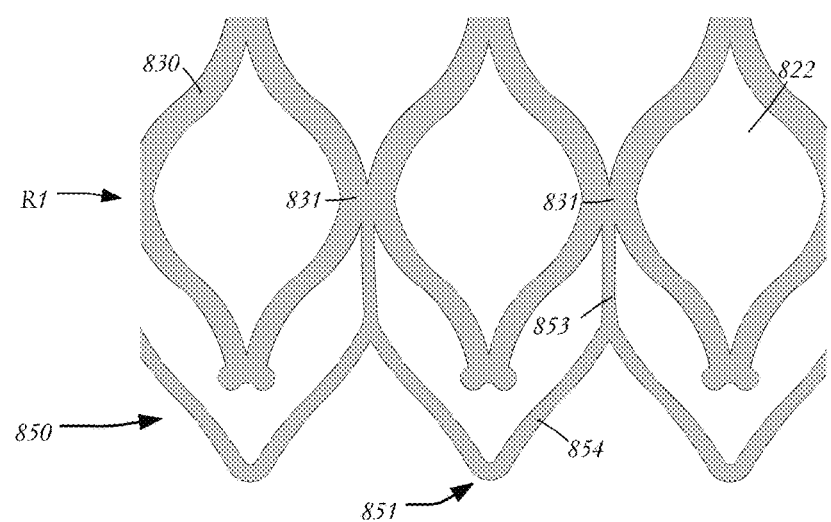
FIG. 8C is a schematic partial side view of the stent of FIG. 8A.

FIGS. 8A-C illustrate yet another variation of stent 606 and includes all the elements described with reference to FIGS. 6A-C. Like-numbered elements of FIGS. 6A-C correspond to like-numbered elements in FIGS. 8A-C, but preceded by an "8" instead of a "6". For example, cells 622 in FIG. 6A correspond to cells 822 in FIG. 8A. In contrast to upper struts 653, upper struts 853 are shortened to reduce the portion of deflecting cells 851 extending past the native valve annulus. In this example, upper struts 853 are approximately 4 mm to 5 mm in length. Further reduction in length may be achieved by shortening upper struts 853, reducing the attachment angle as described with reference to FIGS. 7A-C or removing the upper struts entirely such that the lower struts are directly attached to the nodes.

The preceding embodiments have illustrated several embodiments of projecting struts or deflecting cells capable of pushing a cuff outwardly toward walls of the native valve annulus to seal a heart valve within the annulus. Several configurations of the cuff are also possible as illustrated below. It will be understood that any of the following configurations may be used in conjunction with any of the stent structures described above.

Figure 9A:
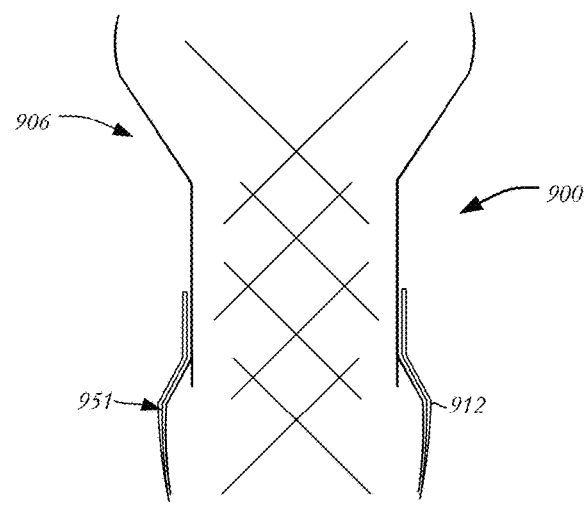
FIGS. 9A and 9B are highly schematic cross-sectional and developed views of portions of a heart valve having an external cuff.
Figure 9B:
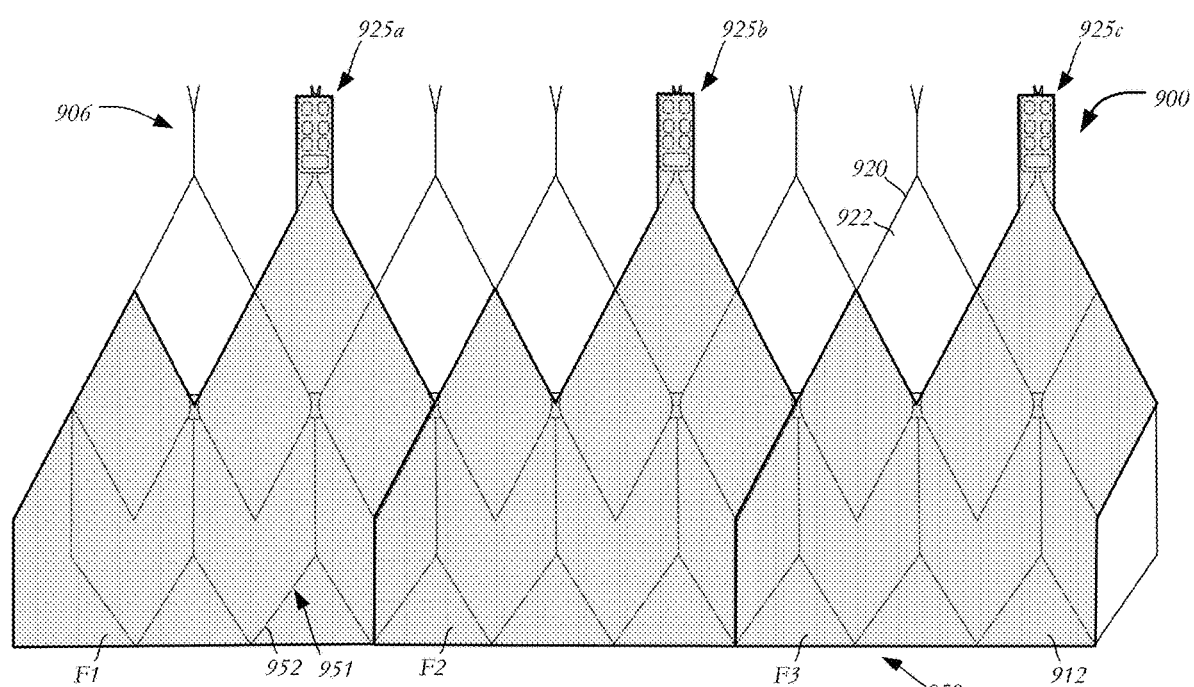

FIGS. 9A and 9B are schematic views of a portion of heart valve 900 including stent 906 with cuff 912 attached to same. For the sake of clarity, leaflets of the valve assembly are not shown. Stent 906 includes a plurality of struts 920 attached together to form diamond-shaped cells 922. Three commissure features 925a, 925b, 925c are also shown attached to struts 920. Stent 906 further includes sealing row 950 formed of a plurality of deflecting cells 951, each deflecting cell being formed of slender struts 952 as discussed above.

Cuff 912 is disposed on the abluminal surface of stent 906 (i.e., FIG. 9 is a schematic illustration of the exterior of heart valve 900). Cuff 912 may be formed of a polymer, a fabric or tissue, such as bovine, porcine, ovine, equine, kangaroo, PTFE, UHMWPE, PET, Dacron, PVA, Polyurethane, silicone or combinations thereof. In this configuration, cuff 912 is formed of three distinct fragments, F1, F2, F3 that are sewn together to ease manufacturability, each fragment corresponding to one of the commissure features 925. It will be understood, however, that cuff 912 may be formed of one, two, three, four or more fragments. Moreover, fragments may be disposed vertically and/or circumferentially, may be formed of the same or different materials and any one or combination of fragments may include other materials such as memory shape materials. In use, when released from a delivery device, deflecting cells 951 radially expand and push external cuff 912 against the walls of the native valve annulus to seal heart valve 900 and reduce paravalvular leakage.

Figure 10A:
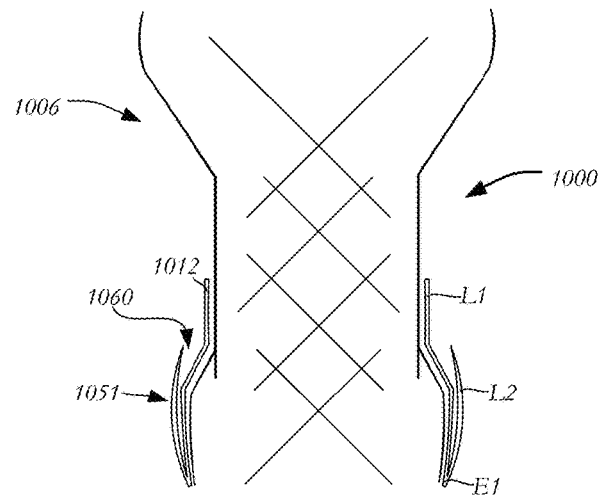
FIGS. 10A and 10B are highly schematic cross-sectional and developed views of portions of a heart valve having a two-layered external cuff.
Figure 10B:
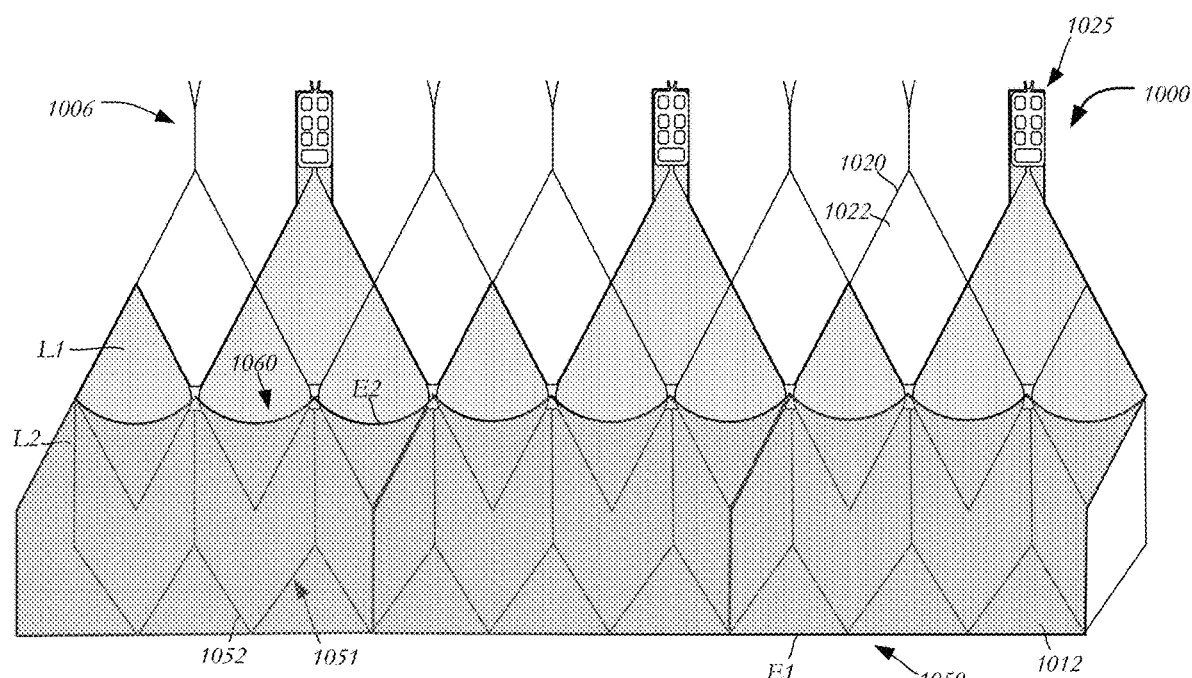

FIGS. 10A and 10B are schematic views of a portion of heart valve 1000 including stent 1006 with cuff 1012 attached to same. Stent 1006 includes a plurality of struts 1020 forming cells 1022 and commissure features 1025. Stent 1006 further includes sealing row 1050 formed of a plurality of deflecting cells 1051, each deflecting cell being formed of slender struts 1052 as discussed above. The main difference between heart valve 900 and heart valve 1000 is that cuff 1012 forms two layers L1, L2 on the abluminal surface. Specifically, a first layer L1 extends from commissure features 1025 to proximal edge E1 of cuff 1012. The cuff is folded over away from stent 1006 to form a second layer L2. Pockets 1060 may be formed between layers L1, L2.

As shown, pockets 1060 formed between layers L1, L2 of cuff 1016 may include open edges E2. During use, blood flowing back toward the proximal end of the heart valve may fill pockets 1060 and expand the pockets to reduce the amount of paravalvular leakage. Alternatively, pockets 1060 may be filled with a liquid, a gel, a powder or other media and closed shut via sutures, adhesive or other known methods to mitigate paravalvular leakage. One example of the filler media may be a solution of polyvinyl alcohol (PVA). As cuff 1012 contacts blood upon the implantation of prosthetic heart valve 1000, the filler media may swell in size, increasing the size and specifically the diameter of the pockets between layers L1, L2. The enlarged pockets thus fill the gaps between the native valve annulus and the prosthetic heart valve, minimizing or preventing paravalvular leakage.

Figure 11A:
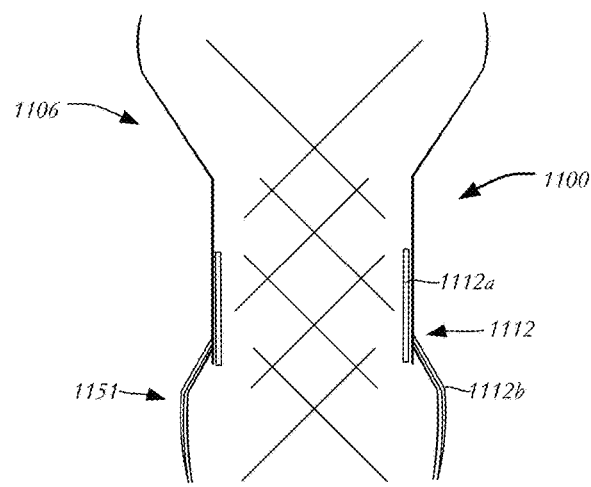
FIGS. 11A and 11B are highly schematic cross-sectional and developed views of portions of a heart valve having a cuff including an upper luminal portion and a lower abluminal portion.
Figure 11B:
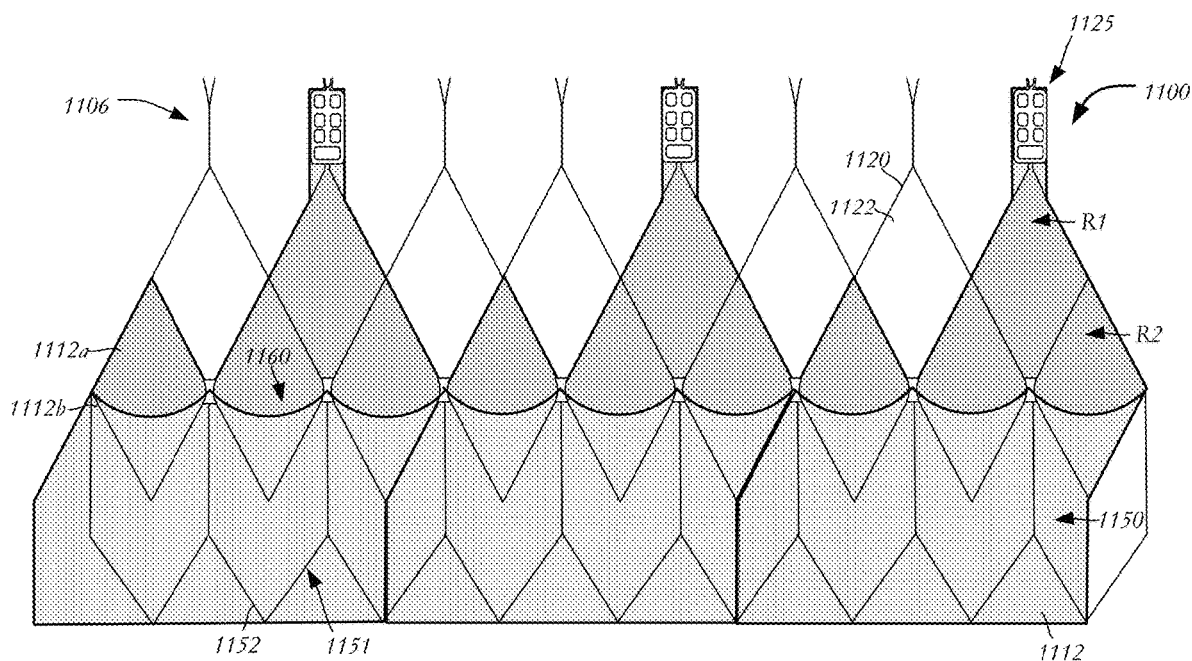

Though the previous embodiments have shown cuffs attached to the abluminal surface of stents (e.g., external surfaces), the configurations are not so limited. FIGS. 11A and 11B are schematic views of a portion of heart valve 1100 including stent 1106 with cuff 1112 attached to same. Stent 1106 includes a plurality of struts 1120 forming cells 1122 and commissure features 1125. Stent 1106 further includes sealing row 1150 formed of a plurality of deflecting cells 1151, each deflecting cell being formed of slender struts 1152.

In this configuration, cuff 1112 is divided into two fragments including an upper portion 1112a and a lower portion 1112b. Upper portion 1112a may be disposed on the luminal surface of stent 1106 and attached thereto, spanning commissure features 1125, cells 1122 in row R1 that are under commissure features 1125 and portions of cells 1122 in row R2. Lower portions 1112b may be disposed on the abluminal surface and extend over the remaining portions of cells 1122 in row R2 and sealing row 1150, covering deflecting cells 1151.

Figure 12A:
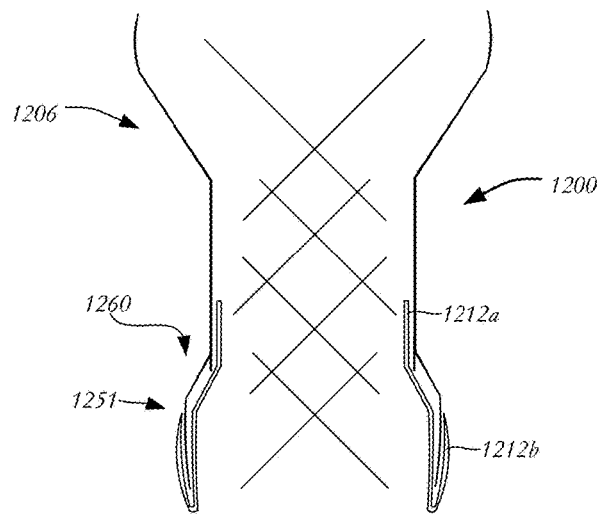
FIGS. 12A and 12B are highly schematic cross-sectional and developed views of portions of a heart valve having a cuff wrapped around the stent from the luminal surface to the abluminal surface.
Figure 12B:
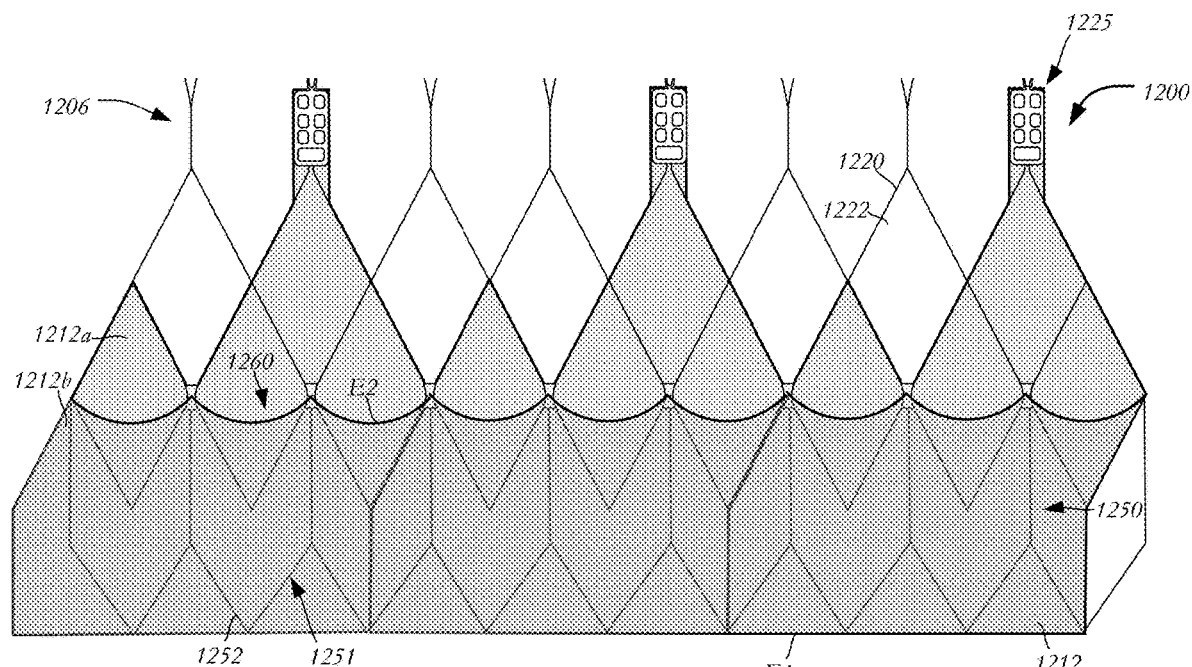

FIGS. 12A and 12B are schematic views of a portion of heart valve 1200 including stent 1206 with wrap-around cuff 1212 attached to same. Stent 1206 includes a plurality of struts 1220 forming cells 1222 and commissure features 1225. Stent 1206 further includes sealing row 1250 formed of a plurality of deflecting cells 1251, each deflecting cell being formed of slender struts 1252.

In this configuration, cuff 1212 is divided into an inner portion 1212a and outer portion 1212b. Inner portion 1212a may be disposed on the luminal surface of stent 1206 and attached thereto, spanning from commissure features 1222 to proximal edge E1. Cuff 1212 may then be wrapped around deflecting cells 1251 and extend distally toward commissure features 1222, forming an outer portion 1212b disposed on the abluminal surface of stent 1206. As shown, outer portion 1212b terminates at edges E2, which may be sutured to inner portion 1212a to form pockets 1260 containing filler media as described above. Alternatively, portions of edges E2 may be kept open so that back-flowing blood enters pockets 1260 and causes the pockets to expand to reduce paravalvular leakage.

Figure 13:
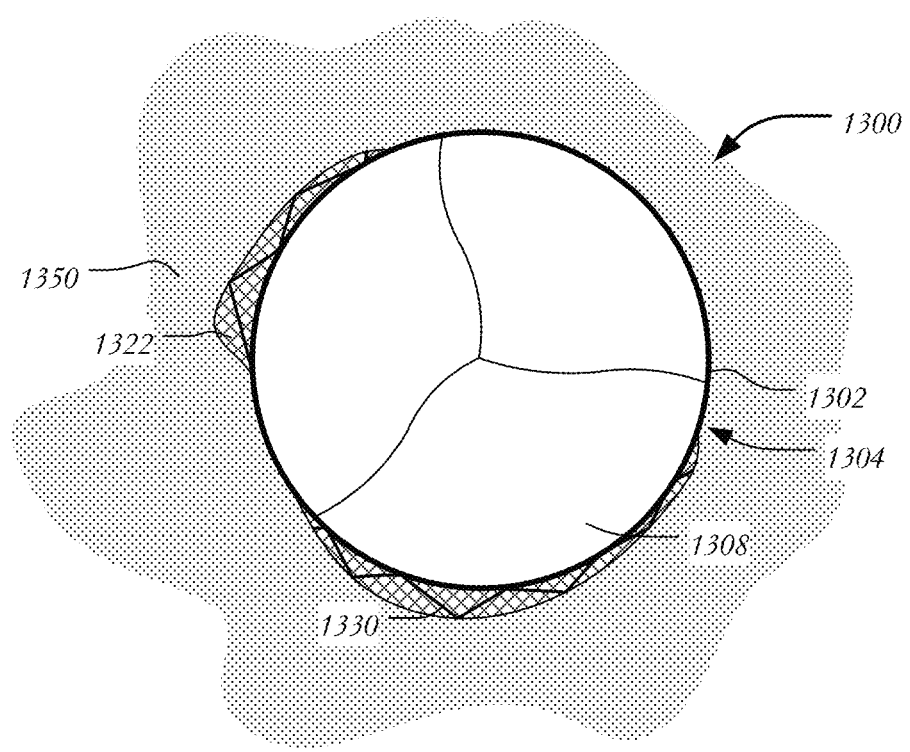
FIG. 13 is a highly schematic cross-sectional view of a heart valve having deflecting cells disposed within a native valve annulus.

FIG. 13 is a highly schematic cross-sectional view showing heart valve 1300 having stent 1302, valve assembly 1304 including leaflets 1308 and a cuff 1322, and deflecting cells 1330 supporting portions of cuff 1322. As seen in FIG. 13, deflecting cells 1330 extend radially outward from stent 1302 to press cuff 1322 into the gaps between heart valve 1300 and native valve annulus 1350. Cuff 1322 may be capable of promoting tissue growth between heart valve 1300 and native valve annulus 1350. For example, cuff 1322 may be innately capable or promoting tissue growth and/or may be treated with a biological or chemical agent to promote tissue growth, further enabling it to seal the heart valve within the native valve annulus. When deflecting cells 1330 are functioning properly, heart valve 1300 will be adequately sealed within native valve annulus 1350 so that blood flows through leaflets 1308 of valve assembly 1304, and so that blood flow through any gaps formed between heart valve 1300 and native valve annulus 1350 is limited or reduced.

While the devices disclosed herein have been described for use in connection with heart valve stents having a particular shape, the stent could have different shapes, such as a flared or conical annulus section, a less-bulbous aortic section, and the like, as well as a differently shaped transition section. Additionally, though the stents and cuffs have been described in connection with expandable transcatheter aortic valve replacement, they may also be used in connection with other expandable cardiac valves, as well as with surgical valves, sutureless valves and other devices in which it is desirable to create a seal between the periphery of the device and the adjacent body tissue.

Moreover, although the disclosures herein have been described with reference to particular embodiments, it is to be understood that these embodiments are merely illustrative of the principles and applications of the present disclosure. For example, in embodiments having deflecting cells, it will be appreciated that each deflecting cell may be capable of independent movement, for example, by providing independent upper struts for each deflecting cell. Deflecting cells also need not be continuous around the perimeter of the annulus section. Instead, a number of deflecting cells may be disposed around the circumference of the annulus section, each deflecting cell being spaced from adjacent ones. Additionally, while the deflecting cells and projecting struts have been shown as being disposed proximal to the annulus section of a stent, such features may instead be disposed adjacent the annulus section or the transition section. Deflecting cells and projecting struts may also be disposed proximal to the annulus section and extend distally toward the aortic section. In other variation, the heart valve need not include all of the section discussed above (e.g., the aortic or transition sections may be eliminated entirely). It is therefore to be understood that numerous modifications may be made to the illustrative embodiments and that other arrangements may be devised without departing from the spirit and scope of the present claims.

In some embodiments, a prosthetic heart valve for replacing a native valve includes a collapsible and expandable stent extending between a proximal end and a distal end. The stent includes an annulus section adjacent the proximal end and having a first diameter, a plurality of first struts forming cells, and a plurality of second struts connected to the annulus section and forming a plurality of deflecting cells expandable to define a second diameter larger than the first diameter. A valve assembly is disposed within the stent and a cuff is coupled to the stent and covers the plurality of deflecting cells.

In some examples, each of the deflecting cells may include upper struts and lower struts, the upper struts being joined to the lower struts at an angle of between about 90 degrees and about 145 degrees; and/or the heart valve may be implantable within a native valve annulus and a portion of the deflecting cells may be disposed below the native valve annulus when implanted; and/or the second diameter may be about 4.0 mm to about 6.0 mm larger than the first diameter in an expanded condition; and/or each of the deflecting cells may include upper struts and lower struts, the upper struts being about 9.0 mm to about 10.0 mm in length; and/or the first struts may have a first thickness and the second struts have a second thickness, the first thickness being greater than the second thickness; and/or the first thickness may be twice as large as the second thickness; and/or the cuff may be formed of multiple fragments; and/or the cuff may be at least partially disposed on an abluminal surface of the stent; and/or the cuff may include a first layer and a second layer, the first layer being disposed on the abluminal surface of the stent and extending from the plurality of commissure features to a proximal edge, the cuff being folded at the proximal edge away from the stent to form a second layer on the first layer; and/or the first layer and second layer may be sutured together to define a plurality of pockets open at second edges, the pockets being configured to expand upon receiving back-flowing blood; and/or the cuff may include a first portion disposed on an abluminal surface of the stent, and a second portion disposed on a luminal surface of the stent; and/or the stent may include a plurality of commissure features and the cuff extends from the plurality of commissure features to the proximal edge on an abluminal surface of the stent, and folds over the deflecting cells so that the second portion is disposed on the luminal surface of the stent.

In some embodiments, a prosthetic heart valve for replacing a native valve includes a collapsible and expandable stent extending between a proximal end and a distal end and an annulus section adjacent the proximal end and having a first diameter. The stent includes a plurality of first struts forming cells, and a plurality of projecting struts joined to proximal-most cells, each of the projecting struts having a free end and an attached end joined to an intersection of first struts. A valve assembly is disposed within the stent and a cuff is coupled to the stent and covering the projecting struts.

In some examples, each of the projecting struts may include an eyelet disposed at the free end; and/or each of the projecting struts is capable of independent movements from others of the projecting struts and/or the projecting struts may be arranged in pairs, each two of the projecting struts being attached to a same intersection of first struts; and/or the projecting struts may be angled between about 15 degrees and about 35 degrees away from a longitudinal axis of the stent; and/or the cuff may be at least partially disposed on an abluminal surface of the stent; and/or the cuff may be at least partially disposed on a luminal surface of the stent.

In some embodiments, a prosthetic heart valve for replacing a native heart valve includes a collapsible and expandable stent having proximal and distal ends, the stent including an annulus section adjacent the proximal end, the annulus section having a first expanded diameter and a first radial spring constant. The stent further includes a plurality of deflecting features which project outwardly from the annulus section when the stent is in an expanded condition, the deflection features having a lower radial spring constant than the first section. A valve is disposed within the annulus section distal to the deflection features, the valve being operative to permit flow toward the distal end of the stent and to substantially block flow toward the proximal end of the stent. The heart valve further includes a cuff, a portion of the cuff being coupled to the deflection features.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve for replacing a native valve, comprising:
a collapsible and expandable stent extending between a proximal inflow end and a distal outflow end, the stent including an annulus section adjacent the proximal end and having a first diameter, an aortic section adjacent the distal end having a larger diameter than the annulus section, a transition section between the annulus section and the aortic section, a plurality of commissure features positioned at a juncture of the annulus section and the transition section, at least one retaining element at the distal end, the at least one retaining element being sized and shaped to cooperate with a retaining structure on a deployment device, a plurality of first struts forming first cells in the annulus section, and a plurality of second struts connected to the annulus section and forming a plurality of second cells expandable to define a second diameter larger than the first diameter, the second cells being positioned nearer the proximal end than are the first cells;
a valve assembly disposed within the stent and coupled to the plurality of commissure features; and
a cuff coupled to the stent and covering the plurality of second cells, the cuff including an abluminal portion disposed on an abluminal surface of the stent, and a luminal portion disposed on a luminal surface of the stent, wherein the luminal portion of the cuff extends from the plurality of commissure features to a proximal edge of the stent, the abluminal portion of the cuff extends from the proximal edge of the stent to a distal edge of the abluminal portion of the cuff, and the distal edge of the abluminal portion of the cuff is sutured to the luminal portion of the cuff to form closed pockets so that the closed pockets do not include any open edges,
the aortic section defining at least one row of aortic cells, the aortic cells being larger than the first cells.

2. The prosthetic heart valve of claim 1, wherein each of the second cells includes upper struts and lower struts, the upper struts being joined to the lower struts at an angle of between about 90 degrees and about 145 degrees.

3. The prosthetic heart valve of claim 1, wherein the heart valve is implantable within a native valve annulus and a portion of the second cells is disposed below the native valve annulus when implanted.

4. The prosthetic heart valve of claim 1, wherein the second diameter is about 4.0 mm to about 6.0 mm larger than the first diameter in an expanded condition.

5. The prosthetic heart valve of claim 1, wherein each of the second cells includes upper struts and lower struts, the upper struts being about 9.0 mm to about 10.0 mm in length.

6. The prosthetic heart valve of claim 1, wherein the first struts have a first thickness and the second struts have a second thickness, the first thickness being greater than the second thickness.

7. The prosthetic heart valve of claim 6, wherein the first thickness is twice as large as the second thickness.

8. The prosthetic heart valve of claim 1, wherein the cuff is formed of multiple fragments.

9. The prosthetic heart valve of claim 1, wherein the luminal portion of the cuff and the abluminal portion of the cuff are continuous, the cuff folding over the second cells at the proximal edge of the stent.

10. The prosthetic heart valve of claim 1, wherein the closed pockets are filled with a filler material that swells upon contact with blood.

11. The prosthetic heart valve of claim 10, wherein the filler material includes polyvinyl alcohol.

12. The prosthetic heart valve of claim 1, wherein the abluminal portion of the cuff is formed of animal tissue.

13. The prosthetic heart valve of claim 12, wherein the animal tissue is porcine tissue.

* * * * *